(12) United States Patent
Burkhard et al.

(10) Patent No.: US 11,510,694 B2
(45) Date of Patent: Nov. 29, 2022

(54) MEDICAL APPARATUS WITH OPTICAL SENSING, AND RELATED DEVICES AND METHODS

(71) Applicant: INTUITIVE SURGICAL OPERATIONS, INC., Sunnyvale, CA (US)

(72) Inventors: Natalie Burkhard, East Palo Alto, CA (US); John Ryan Steger, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 234 days.

(21) Appl. No.: 16/636,500

(22) PCT Filed: Aug. 10, 2018

(86) PCT No.: PCT/US2018/046251
§ 371 (c)(1),
(2) Date: Feb. 4, 2020

(87) PCT Pub. No.: WO2019/032984
PCT Pub. Date: Feb. 14, 2019

(65) Prior Publication Data
US 2020/0246033 A1 Aug. 6, 2020

Related U.S. Application Data
(60) Provisional application No. 62/544,427, filed on Aug. 11, 2017.

(51) Int. Cl.
*A61B 17/29* (2006.01)
*A61B 90/00* (2016.01)
(Continued)

(52) U.S. Cl.
CPC ............ *A61B 17/29* (2013.01); *A61B 90/361* (2016.02); *A61B 34/76* (2016.02);
(Continued)

(58) Field of Classification Search
CPC .................. A61B 17/29; A61B 90/361; A61B 2090/0807; A61B 2017/00075; A61B 2017/00907; A61B 2017/2926
See application file for complete search history.

(56) References Cited

U.S. PATENT DOCUMENTS

2002/0107517 A1    8/2002   Witt et al.
2006/0217697 A1    9/2006   Lau et al.
(Continued)

FOREIGN PATENT DOCUMENTS

EP           2818122 A1    12/2014
WO    WO-02058542 A2    8/2002
(Continued)

OTHER PUBLICATIONS

International Search Report and Written Opinion for Application No. PCT/US2018/046251, dated Feb. 1, 2019, 17 pages.
(Continued)

*Primary Examiner* — Brooke Nicole Labranche
(74) *Attorney, Agent, or Firm* — Jones Robb, PLLC (57) ABSTRACT

A medical apparatus can include an instrument comprising a shaft and a jaw assembly coupled to an end of the shaft; an image capture device; and a controller operably coupled to the image capture device to receive image data from the image capture device. The image data is from images of material gripped between jaw members of the jaw assembly and captured by the image capture device, with the controller programmed to process the received image data using at least one of optical flow and digital image correlation. A medical apparatus can include an instrument comprising a
(Continued)

shaft, and a jaw assembly coupled to an end of the shaft, the jaw assembly comprising a pair of jaw members having opposing surfaces configured to grasp material between the opposing surfaces, wherein at least a portion of the opposing surface of a first jaw member of the pair of jaw members is transparent.

22 Claims, 4 Drawing Sheets

(51) Int. Cl.
    *A61B 34/00*     (2016.01)
    *A61B 17/00*     (2006.01)

(52) U.S. Cl.
    CPC ............... *A61B 2017/00075* (2013.01); *A61B 2017/00907* (2013.01); *A61B 2017/2926* (2013.01); *A61B 2090/0807* (2016.02)

(56) References Cited

U.S. PATENT DOCUMENTS

| | | | |
|---|---|---|---|
| 2013/0253489 A1* | 9/2013 | Nau, Jr | A61B 18/18 606/17 |
| 2015/0327931 A1 | 11/2015 | Chernov et al. | |
| 2016/0157883 A1 | 6/2016 | Hissong et al. | |
| 2016/0262750 A1* | 9/2016 | Hausen | A61B 17/32 |
| 2017/0143260 A1 | 5/2017 | Latimer et al. | |
| 2017/0181797 A1 | 6/2017 | Nau, Jr. et al. | |
| 2017/0296178 A1 | 10/2017 | Miller et al. | |
| 2018/0049822 A1 | 2/2018 | Henderson et al. | |

FOREIGN PATENT DOCUMENTS

| | | |
|---|---|---|
| WO | WO-2010147766 A1 | 12/2010 |
| WO | WO-2012158774 A1 | 11/2012 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European search report for EP application No. 18844411.1 dated Aug. 5, 2020, 10 pages.

\* cited by examiner

MEDICAL APPARATUS WITH OPTICAL SENSING, AND RELATED DEVICES AND METHODS

CROSS-REFERENCE TO RELATED APPLICATIONS/CLAIM FOR PRIORITY

This application is a U.S. national stage application under 35 U.S.C. § 371 (c) of International Application No. PCT/US2018/046251, filed Aug. 10, 2018, which claims the benefit of priority to U.S. Provisional Application No. 62/544,427, filed Aug. 11, 2017, each of which is hereby incorporated by reference herein in its entirety.

TECHNICAL FIELD

The present disclosure relates to medical apparatuses that include optical sensing technology, and related devices and methods. In various aspects, the present disclosure relates to the use of optical sensing technology for control over minimally invasive surgical instruments.

INTRODUCTION

Endoscopic medical procedures, such as various surgical, treatment, and/or diagnostic procedures (collectively referred to herein as "surgical" procedures), are performed by inserting one or more instruments through a small incision or through narrow endoscopic tubes (cannulas) inserted through a small entrance wound in the skin or through a naturally occurring orifice. Endoscopic medical procedures can be performed both manually (e.g., laparoscopically) or by using teleoperated computer-assisted systems (sometimes referred to as robotic surgery).

Endoscopic procedures often require the clinician to manipulate organs, vessels, and other tissues (all of which are referred to herein as "tissue" for simplicity) at locations remote from the incision. Such manipulation can include, but is not limited to, for example, gripping, clamping, suturing, separating, retracting, ablating, probing, and cutting. The ability to manipulate tissue in a controlled manner is desirable. For instance, in some procedures, it is desirable to firmly grip tissue, for example with a jaw assembly of an instrument end effector, in a stable manner while further action, such as cutting, sealing, stapling, or the like, is performed. A stable grip on the tissue avoids gripping the tissue so hard that it is excessively deformed (e.g., stretched and/or crushed), while gripping it with enough force to inhibit the tissue from slipping out of the grip of the jaws.

The ability to sense the nature of a particular type of manipulation of tissue, for example the degree of gripping of tissue, is thus desirable to facilitate a surgeon performing an endoscopic procedure. Sensing tissue movement and/or deformation during manipulation with an end effector, however, can pose challenges that are not encountered when sensing movement between two rigid objects. Accordingly, some conventional mechanisms for sensing motion between two rigid objects may not be well-suited for endoscopic procedures. For example, various vibrational-based sensing techniques are not well-suited to determine the nature of a tissue manipulation, such as stability of a grip on tissue, because of the conformable, flexible, and wet properties of tissue. Thus, there exists a need to provide techniques and devices for sensing the nature of and effects on tissue being manipulated during various surgical procedures. There also exists a need to provide feedback to a surgeon regarding such sensing. Further, a need exists to provide techniques for automatic control of an endoscopic surgical procedure based on such sensed information.

SUMMARY

Exemplary embodiments of the present disclosure may solve one or more of the above-mentioned technical challenges and/or may demonstrate one or more of the above-mentioned desirable features. Other features and/or advantages may become apparent from the description that follows.

In various exemplary embodiments, the present disclosure contemplates a medical apparatus can include an instrument comprising a shaft and a jaw assembly coupled to an end of the shaft; an image capture device; and a controller operably coupled to the image capture device to receive image data from the image capture device. The image data is from images of material gripped between jaw members of the jaw assembly and captured by the image capture device, with the controller programmed to process the received image data using at least one of optical flow and digital image correlation.

In various other exemplary embodiments, the present disclosure contemplates a medical apparatus comprising an instrument comprising a shaft, and a jaw assembly coupled to an end of the shaft, the jaw assembly comprising a pair of jaw members having opposing surfaces configured to grip material between the opposing surfaces, wherein at least a portion of the opposing surface of a first jaw member of the pair of jaw members is transparent.

In yet other exemplary embodiments, the present disclosure contemplates a medical apparatus comprising an instrument comprising a shaft and a jaw assembly coupled to the shaft, the jaw assembly having a gripping region defined between a pair of jaw members of the jaw assembly. The medical apparatus further comprises an image capture device in the jaw assembly, the image capture device positioned to capture images in the gripping region.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and following detailed description are exemplary and explanatory only and are not restrictive of the claims; rather the claims should be entitled to their full breadth of scope, including equivalents.

Further, to the extent consistent, any of the aspects described herein may be used in conjunction with any or all of the other aspects described herein.

BRIEF DESCRIPTION OF DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. In addition, in some in various instances, similar or the same numbers in two or more figures may be used to represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. Mathematical and geometric terms are not necessarily intended to be used in accordance with their strict definitions unless the context of the description indicates otherwise, because a person having ordinary skill in the art would understand that, for example, a substantially similar element that functions in a substantially similar way could easily fall within the scope of a descriptive term even though the term also has a strict definition.

Various exemplary embodiments of the present disclosure contemplate systems, methods, and devices that can be used to sense, via optical sensing, the nature of tissue manipulation, and consequent effect on the manipulated tissue, occurring during use of a surgical instrument end effector performing a surgical procedure. By using image capturing and processing capabilities for the optical sensing, information regarding tissue movement and/or deformation (or other effects on the tissue relating to tissue manipulation) can be accurately determined, allowing for better control of the tissue manipulations being performed. Tissue manipulations that may benefit from stable gripping control, include, but are not limited, to, stapling, suturing, moving of tissue from one position to another, and other tissue manipulations those having ordinary skill in the art would be familiar with.

In accordance with various exemplary embodiments, the present disclosure contemplates surgical instruments comprising end effectors having jaw members that open and close relative to each other, with a gripping region being defined between opposing surfaces of the jaw members. Such a jaw assembly is configured to grip tissue as the jaw members are approximated (moved toward each other). For training and/or testing purposes, the exemplary surgical instruments described herein can also be used on materials having properties similar to tissue. Moreover, those having ordinary skill in the art would appreciate that the principles and exemplary embodiments disclosed herein may be used in applications outside of medical and surgical applications where stable gripping of material and/or the ability to determine movement or deformation of material (such as may occur during gripping or otherwise manipulating material) may be desired, particularly when the material is flexible, conformable, and/or elastic. Applications outside of the medical and surgical fields may include, for example, other manufacturing or robotic applications in which handling of materials in a controlled and stable manner, without excessive deformation or slip, is desirable, such as, for example, in the food services industry.

Figure 1:
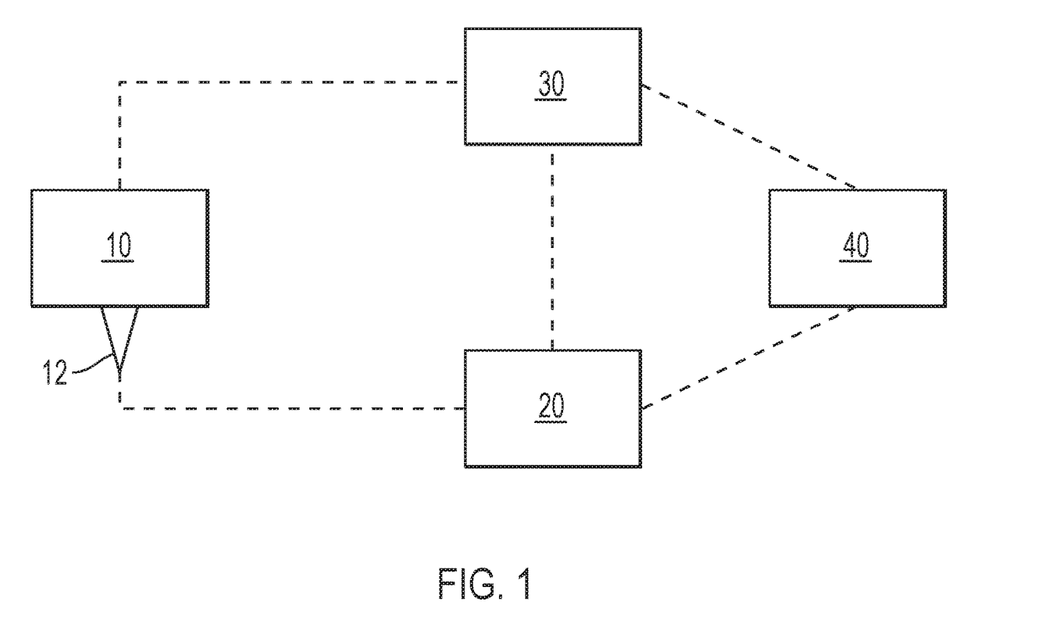
FIG. 1 is a block diagram illustrating components of a medical system according to an exemplary embodiment of the present disclosure.

With reference to FIG. 1, a block diagram of various exemplary components of a medical apparatus employing optical sensing technology in conjunction with a surgical instrument in order to sense tissue motion (for example, relative to the end effector of the surgical instrument or via deformation of the tissue), during endoscopic procedures performed using the surgical instrument is depicted. The system includes a surgical instrument 10 operably coupled to an optical sensing module 20 and a controller 30, the latter two components also being operably coupled to each other. In various exemplary embodiments, the surgical instrument 10 has an end effector 212 that is configured to perform various tissue manipulations during a surgical procedure. The optical sensing module 20 includes one or more components operably coupled to the surgical instrument 10 to sense information from tissue being manipulated by the end effector of the surgical instrument and to provide data regarding the sensed information to the controller 30. The controller 30 includes one or more processing devices programmed to calculate motion and/or deformation of the tissue based on the data. In various exemplary embodiments, the controller 30 also may be programmed to output feedback regarding the tissue motion and/or deformation, and/or provide control over the surgical instrument 10 based on the received data. The system also may optionally include one or more feedback mechanisms 40 operably coupled to the controller and/or the optical sensing module 20 to provide feedback by a user of the system regarding the information sensed by the optical sensing module 30 and/or other output based on the sensed information processed by the controller 30.

Although controller 30 is depicted in FIG. 1 and described in other exemplary embodiments as a separate component, those having ordinary skill in the art would appreciate that one or more of its processing functions and devices can be distributed as separate components, including as components making up a part of the optical sensing module, surgical instrument, and/or feedback mechanism. By way of example, some processing of the sensed data from the optical sensing module can occur at a processor that is part of the optical sensing module, such as being part of an image capture device as is described further below.

Figure 2:
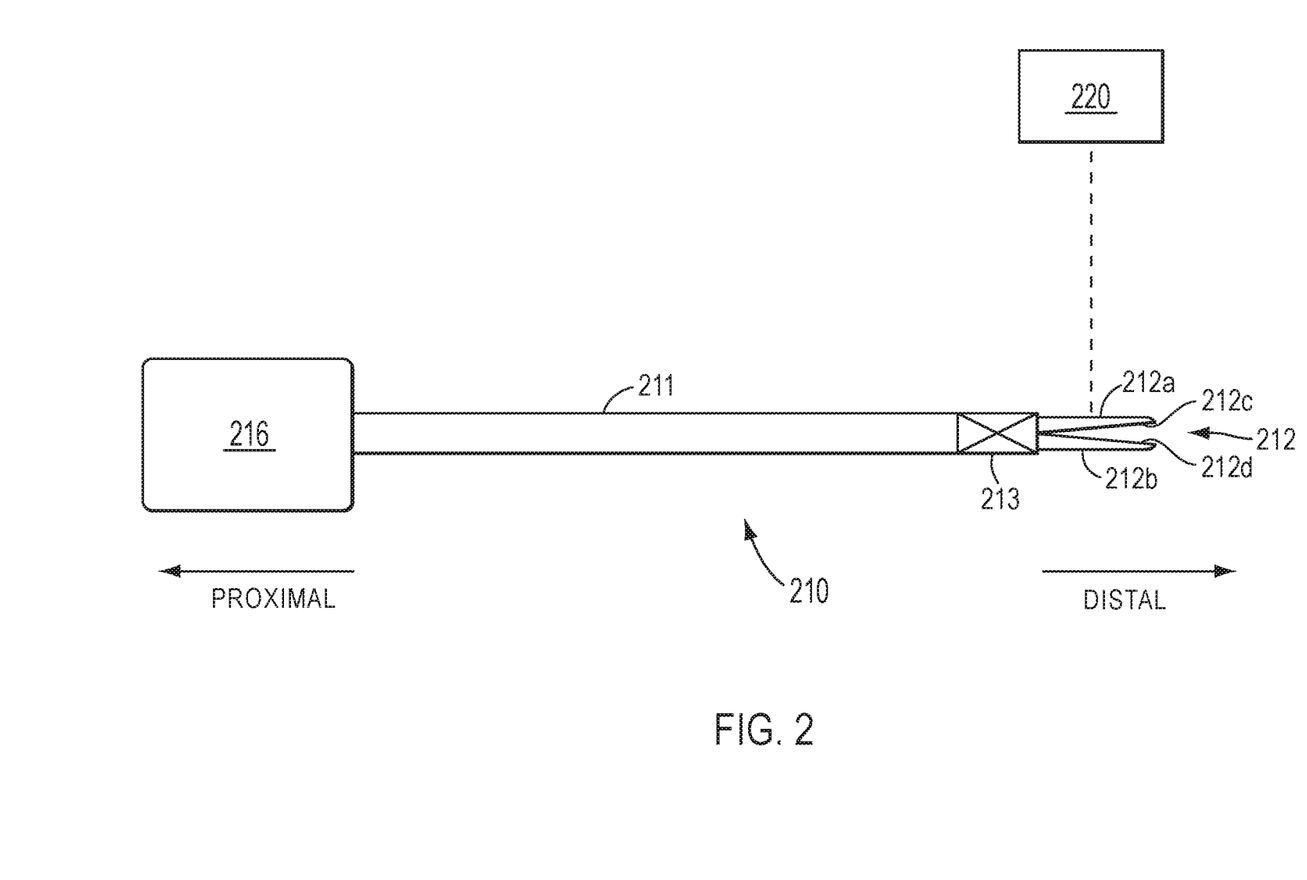
FIG. 2 is a schematic perspective view of a surgical instrument in accordance with various exemplary embodiments of the present disclosure.

FIG. 2 is a schematic perspective view of an exemplary embodiment of a surgical instrument that can be used in the system of FIG. 1, and in other systems and methods described herein. Relative proximal and distal directions as defined relative to the instrument are depicted by the arrows in the figure. The surgical instrument 210 includes a shaft 211 with an end effector 212 coupled at a distal end of the shaft 211. One or more optional articulating joint members 213 (e.g., wrist mechanisms) can couple the end effector 212 to the shaft 211. Alternatively, the end effector 212 can be coupled directly to the shaft 211 (not shown in FIG. 1). As depicted in FIG. 2, in various exemplary embodiments, the end effector 212 comprises a jaw assembly including jaw members 212a, 212b configured to move away and toward each other (open and close). The jaw members 212a, 212b have opposing gripping surfaces 212c, 212d that define a gripping region therebetween such that as the jaw members 212a, 212b are approximated they can grip tissue, as is readily understood by those having ordinary skill in the art. In exemplary embodiments of the present disclosure, both jaw members of a jaw assembly may be movable relative to each other, or one jaw member may be fixed and the other moveable. Instruments that use an end effector comprising a jaw assembly include, but are not limited to, for example, vessel sealers (using electrode surfaces on the jaws to provide electrosurgical energy to grasp tissue), staplers, forceps, clamps, and cutting tools, or combinations thereof.

Coupled to the proximal end of the shaft 211 is a backend transmission mechanism 216 comprising one or more drive members (e.g., gears, rotating shafts, levers, etc.) to convert input at the backend transmission mechanism 216 to the various drive members and along actuation elements (e.g., rods, cables, or other types of tension/compression members (not shown)) extending down the shaft. In this manner input at the transmission mechanism 216 can be transmitted as force to actuate motion of the shaft, end effector components, and optional joint members. For manually operated surgical instruments, the backend transmission mechanism 216 may comprise a handle with various triggers, buttons, and other input devices operable by a user of the instrument. Alternatively, for surgical instruments configured for use in teleoperated computer-assisted surgical systems (sometimes referred to as robotic surgical systems), the backend transmission mechanism 216 has an interface for operably engaging with various drive mechanisms at a patient side cart that holds the surgical instrument during a surgical procedure, which drive mechanisms are operable via servomotors. Examples of teleoperated computer-assisted surgical systems for which various exemplary embodiments of the present disclosure may be used include, but are not limited to, the daVinci® Surgical Systems.

As further depicted in the box diagram components of FIG. 2, an optical sensing module 220 (as in FIG. 1), exemplary embodiments of which are described in further detail below, can be operably coupled to sense information regarding movement and/or deformation of tissue captured between the jaw members 212a, 212b.

Figure 3:
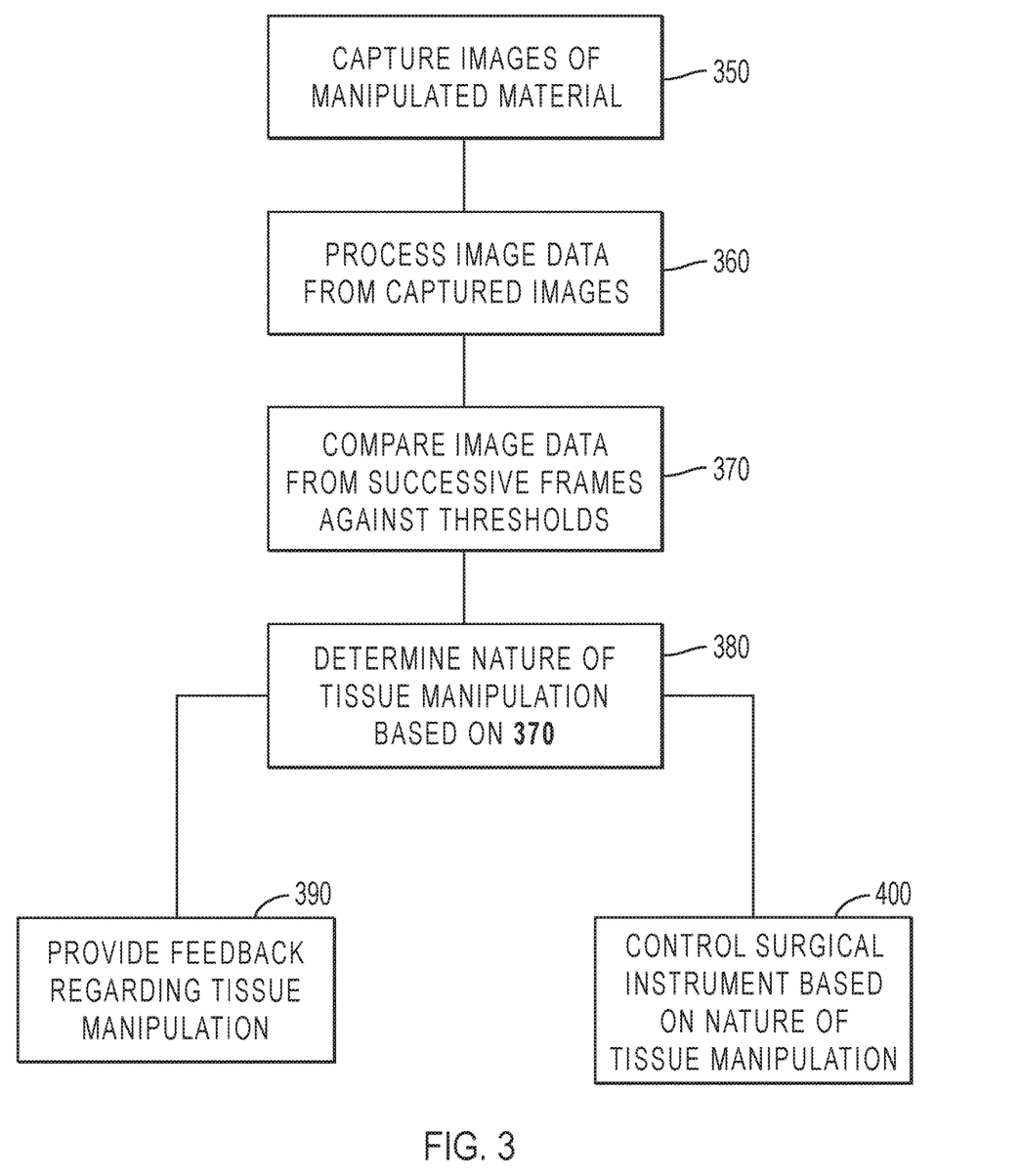
FIG. 3 is a flow diagram depicting exemplary parts of a process for control of surgical procedure based on sensing tissue motion.

Referring again to FIG. 1, and also with reference to the exemplary workflow depicted in FIG. 3, in various exemplary embodiments, the optical sensing module 20 comprises an image capture device that is positioned so as to capture images of tissue being manipulated by the surgical instrument (e.g., tissue gripped between the jaw members of a jaw assembly of the surgical instrument 10) (350 in workflow of FIG. 3). In an exemplary embodiment, using the image data captured by the image capture device, the system can sense (calculate) information regarding movement and/or deformation of the material being manipulated (e.g., tissue gripped by a jaw assembly), illustrated at 360 in the exemplary workflow of FIG. 3. For example, the system controller 30 can be programmed to process image data received from the image capture device using optical flow and/or digital image correlation techniques. As those of ordinary skill in the art would understand, optical flow involves estimations regarding motion of an object by comparing a sequence of captured images. In various exemplary embodiments of the present disclosure, such comparison can include comparing the positions of edges and other characteristic features of the tissue (e.g., held between jaw members of an end effector) in image frames from a sequence of captured images. Processing of the image data using optical flow in computational vision may include, but is not limited to, for example, calculating instantaneous image velocities and/or discrete image displacements. Digital image correlation uses tracking and image registration methods for 2D and/or 3D measurements of changes in images. Its application here may rely on a comparison of pixel array intensities of a sequence of at least two captured images in order to calculate deformation, displacement, strain, etc. of the grasped material.

Nonlimiting examples of image capture devices that are suitable for use in optical flow and/or digital image correlation processing techniques include a pixel sensor or image sensor array, a charged coupled device, and/or an endoscope, which in various exemplary embodiments may utilize such sensors or have other imaging devices associated with it. When selecting image capture devices suitable for use in various exemplary embodiments, it is desirable to select devices having relatively high resolution, shorter focal lengths (which can help to reduce overall size), and/or relatively fast frame rates. Moreover, light sources may be selected so as to enhance the contrast of features of the material being observed (e.g., tissue). In some exemplary embodiments, image post-processing may be utilized to address any shortcomings in the image capture device ability to achieve the desired characteristics noted above.

As mentioned above, the surgical system of FIG. 1 optionally includes a feedback mechanism 40, which can include, among other things, a display. The display can be operably coupled to the image capture device of the optical sensing module 20 and display to a user images captured by the image capture device. The surgical system optionally also may include a storage media, which can be part of the control system, image capture device or a separate module (not shown). The use of storage media can facilitate surgeon training, for example by using stored image data of grasped tissue to provide information regarding how a surgeon's actions affect outcomes of tissue manipulation. Storage of image data also may be used to study tissue pathology during gripping and in comparison with subsequently damaged tissue. It also may be possible to merge the stored image data with preoperative images (e.g. MRI, CT) so as to be able track what tissue has been gripped previously when making determinations of future procedures.

In various exemplary embodiments, based on the processing of the captured image data, the controller 30 is programmed to determine the nature of the tissue manipulation occurring at the end effector and the effect on the tissue; for example, if tissue gripped by a jaw assembly is slipping, excessively deforming, or alternatively is being stably gripped. For example, successive image frames can be compared for changes to determine if threshold levels of changes occur or are exceeded (370 in FIG. 3) so as to lead to a determination of the nature of the tissue manipulation occurring (380 in FIG. 3). For example, in a tissue gripping application using a jaw assembly, movement and/or deformation can be determined based on the comparison to indicate whether tissue is moving (slipping) relative to the jaw assembly and/or being excessively deformed (e.g., crushed or stretched). This information may also be used to determine whether adequate tissue-jaw contact is achieved to enable a stable grip of the tissue.

To make these determinations, exemplary embodiments compare the speckle pattern (an inherent characteristic of tissue) in successive frames of captured images, processing the image data to compare differences in the speckle pattern, which can include either relative shifts in movement or appearance of the speckles within the pattern (which may be indicative of excessive deformation for example) or whole translation shifts of the entire pattern relative to fixed points of the captured image (which may be indicative of tissue slip). In various exemplary embodiments, the present disclosure contemplates the use of an injectable tracer that may be used to track blood flow during the optical imaging in accordance with various exemplary embodiments of the present disclosure. Use of such a tracer may provide additional useful information, such as, for example, relating to perfusion of grasped tissue, flow patterns, etc.

For example, local tissue movement (i.e., movement of tissue gripped between jaws of a jaw assembly) can arise from any combination of motion, including rigid body motion such as translation and rotation, and flexible body motion such as dilations, extension, shear, and other deformation. The surgeon feedback provided and/or the control schemes imposed can differ based on the nature of the motion. For example, translation typically is associated with slip or loss of stable grip and thus a control that corrects the slip and/or provides corresponding feedback, may be warranted. Deformation, on the other hand, may be tolerated to a certain level (e.g., threshold), which if sensed may then be subject to corrective control. The image processing methods discussed above (e.g., DIC and optical flow) serve the purpose of describing the motion of pixels in the image (in some cases, sub-pixels can be sensed, depending on the algorithm), producing a vector field of displacements. The components of motion and deformation can then be extracted from the overall motion from the vector field of displacements. In an exemplary embodiment, this may be accomplished by fitting an affine transformation and estimating the components of movement of interest, (e.g., translation, rotation, dilation, stretch, etc.)

The controller 30 also can be programmed to output commands to the surgical system to provide various feedback (shown at 390 in FIG. 3) based on the processing of the images using optical flow and/or digital image correlation techniques and the subsequent determination of the nature of the tissue manipulation. For example, in a grasping application, if unacceptable levels of tissue slip are determined based on the image processing, the controller may be programmed to cause the system to provide haptic, aural, or visual feedback to a user. For example, the display 40 may display visual feedback indicating tissue is slipping in the jaw assembly, or a visual display may indicate with a colorbar or similar some measure of grasp stability or likelihood of slip. Alternatively, or in addition, aural feedback signifying a warning regarding slip of tissue in the grasper may be provided. Alternatively, or in addition, feedback indicating a stable grip and/or an excessive grip that is causing undesirable tissue deformation may be provided. Haptic feedback also may be provided to the user, such as by the controller 30 being programmed to cause a vibration, skin stretch, or other type of force, kinesthetic, or haptic feedback to the user through the surgical instrument 10.

By way of nonlimiting example, the controller 30 may be programmed to provide a feeling to a user of a hard stop or stiff spring either as part of a virtual environment when attempting to pull back on gripped tissue to a dangerous extent, or as additional resistance when attempting to grasp harder than is deemed safe.

Aside from providing feedback, and as depicted at 400 of the exemplary workflow of FIG. 3, the controller 30 can be used to send commands to the surgical system to automatically control the operation of the surgical instrument 10 based on the processing of the data provided to the controller from the optical sensing module 20 (e.g., image data provided by an image capture device). For example, if the controller determines that the tissue is not stably gripped (e.g., is slipping to an unacceptable level or is being excessively deformed), then the controller 30 can prevent further actuation of a jaw assembly of a surgical instrument, including overriding input by a user to actuate the surgical instrument to perform surgical procedures using the instrument that may require a stable grip of the tissue. In various exemplary embodiments, the controller 30 may be programmed to alter a grip of a jaw assembly of a surgical instrument. For example, the controller 30 may send a command to provide a higher gripping force if tissue slipping is determined. Alternatively, the controller 30 may send a command to release the jaw assembly grip on the tissue if either excessive deformation or tissue slip is determined.

Other possible system responses include relaxing the system back to a prior position if incipient slip is detected.

In accordance with various exemplary embodiments, an optical sensing module including an image capture device can be integrated as part of the surgical instrument itself or can be provided as a separate device used in conjunction with the surgical instrument. Exemplary embodiments of such arrangements are illustrated respectively in FIGS. 4 and 5.

Figure 4:
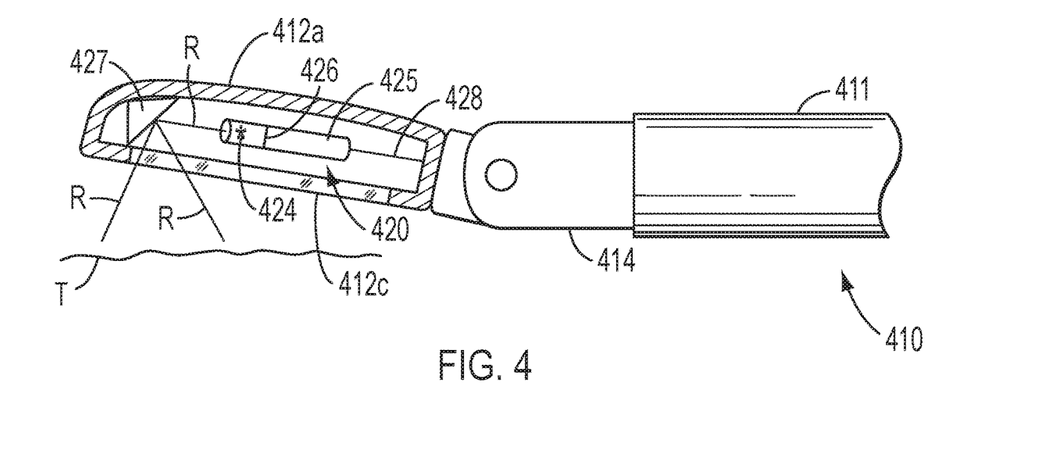
FIG. 4 is a schematic perspective view of a surgical instrument and integral optical sensing module including an image capture device in accordance with an exemplary embodiment of the present disclosure.

Referring to FIG. 4, a schematic partial cut-away perspective view of a surgical instrument with an integral optical sensing module including an image capture device is illustrated. For ease of illustration, only a single jaw member of the jaw assembly of the surgical instrument is depicted. The described mechanisms and components may be included in both jaws for redundancy or to obtain truer measures of tissue deformation if the grasper is intended to grasp thicker specimens. As shown, the surgical instrument 410 comprises a jaw assembly pivotably coupled to a clevis 414 that in turn is directly connected to a distal end of the surgical instrument shaft 411 (although as discussed above an optional wrist mechanism can couple the jaw assembly to the shaft). The jaw assembly has at least one jaw member 412a that has a hollow construction that provides room for housing components of an optical sensing module 420 including an image capture device 425, which can be any of the type of image capture devices discussed herein. To allow for light to be transmitted through the jaw member 412a between the image capture device 425 and an object, such as tissue (labeled T in FIG. 4) for example, positioned in the gripping region between the jaw members, a portion or the entire gripping surface 412c of the jaw member 412a is transparent. For example, in various exemplary embodiments, the jaw member 412a may include a sheet of rigid plastic or glass material held in an opening in the remaining opaque (e.g., metal) frame of the jaw member 412a, or clear material is injection molded and/or bonded to the jaw frame. A suitably strong clear material may also be used for the entirety of the jaw. In the schematic depiction in FIG. 4, the opaque portion of the jaw member frame is indicated by the hatchings and the transparent portion is unhatched. The jaw assembly can be sized to fit within a standard laparoscopic trocar for minimally invasive surgery and/or teleoperated computer-assisted surgery; if serving another application, similar size requirements may apply. The transparent portion of the jaw in an exemplary embodiment can be as large as possible while permitting sufficient use (e.g., strength etc.) of the jaw as a grasping instrument.

The view of FIG. 4 illustrates internal components of the endoscopic image capture device 425 which may include one or more light sources 424, one or more-pixel sensor arrays or charge coupled devices (labeled 426), and one or more optional optical components (prisms, reflecting surfaces, lenses, filters etc.) to alter the path and/or properties of light transmitted to and detected from the tissue T. In the exemplary embodiment depicted, a 90 degree reflecting surface 427 (e.g., mirror) can be positioned to turn light, shown schematically as ray's R in FIG. 4, as so as to be directed between the image capture device 425 and the tissue T.

Circuitry, such as for transmission of data and power to and from the image capture device 425 and shown for simplicity by reference numeral 428, can be routed through the instrument to appropriate connections with external equipment in a manner similar to circuitry used with various minimally invasive electrosurgical instruments, as would be understood by those having ordinary skill in the art. To save space within the instrument and simplify the structure, data and power can be routed through the same wire. In another exemplary embodiment, the wire(s) could be routed external to the instrument and loosely encapsulated within a silicone (or similar) sleeve. In yet other exemplary embodiments, wireless transmission (e.g., via RFID, radio, ZigBee, Bluetooth, etc.) of data and/or power can be employed.

Figure 5:
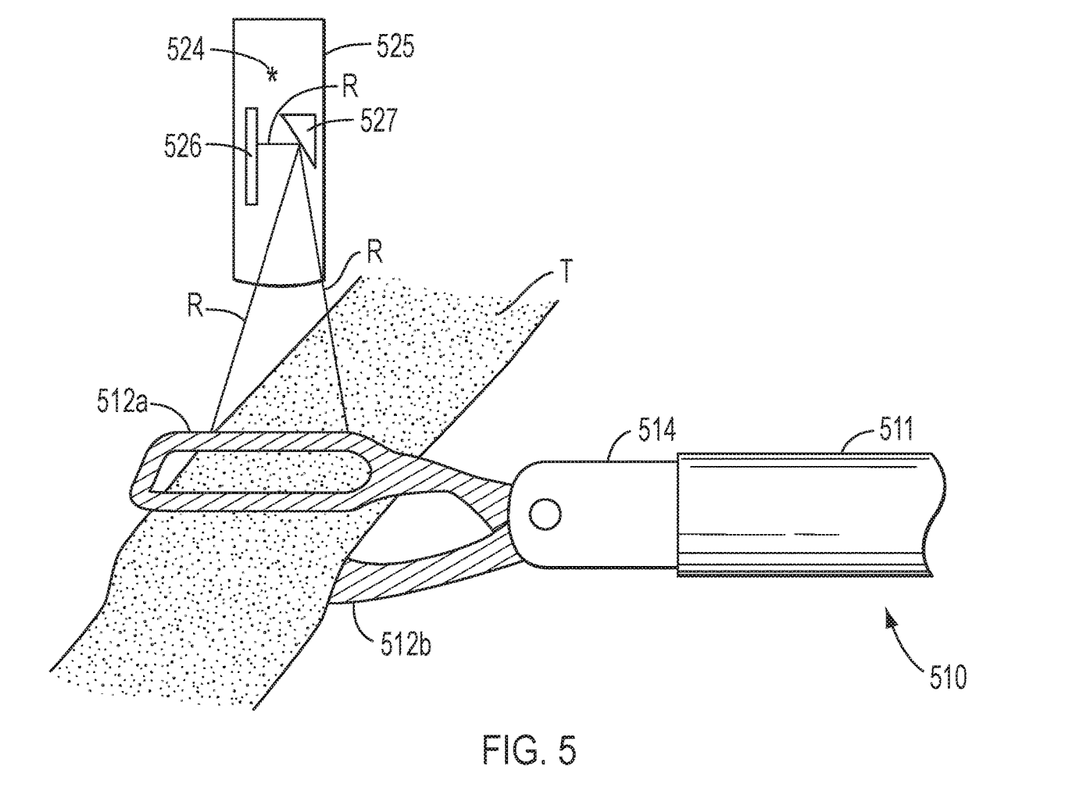
FIG. 5 is a schematic perspective view of a surgical instrument with an optical sensing module including an image capture device in accordance with an exemplary embodiment of the present disclosure.

With reference now to FIG. 5, a schematic perspective view of an exemplary embodiment of a surgical instrument operably coupled to an optical sensing module that includes an image capture device separate from the surgical instrument is illustrated. In the illustration, only a single jaw member of the jaw assembly of the surgical instrument can be fully seen because of the tissue T shown positioned in the gripping region between the jaw members. As shown, the surgical instrument 510 comprises a jaw assembly pivotably coupled to a clevis 514 that is, in turn, directly connected to a distal end of the surgical instrument shaft 511 (although as discussed above an optional wrist mechanism can couple the jaw assembly to the shaft). The jaw assembly has at least one jaw member 512a that is transparent over a portion of the length of the jaw member 512a and through a thickness of the jaw member 512a so as to allow for light to be transmitted through the jaw member 512a between an image capture device 525 and an object, such as the tissue T in FIG. 5. The length of the jaw member is measured along the longitudinal direction in which the jaw member extends distally from the instrument shaft, and the thickness is measured in a direction transverse to the longitudinal direction. In various exemplary embodiments, the jaw member 512a may include a rigid plastic or glass material held in an opening in that penetrates the thickness of the jaw member 512a and that is surrounded by the remaining opaque (e.g., metal) frame of the jaw member 512a. In the schematic depiction in FIG. 5, the opaque portion of the jaw frame is indicated by the hatchings and the transparent portion is unhatched.

The image capture device 525 may be a device such as an endoscope inserted through the same incision or body orifice, or through a separate incision or body orifice, and positioned so as to be able to illuminate and capture images through the transparent portion of the jaw member 512a. The view of FIG. 5 illustrates internal components of the endoscopic image capture device 525 which may include one or more light sources 524, one or more pixel sensor arrays or charge-coupled devices (labeled 526), and one or more optional optical components (prisms, reflecting surfaces, lenses, filters etc.) to alter the path and/or properties of light transmitted to and detected from the tissue T. In the exemplary embodiment depicted, a 90 degree reflecting surface 527 (e.g., mirror) can be positioned to turn light, shown schematically as rays R in FIG. 5, as so as to be directed between the sensor 526 of the image capture device 525 and the tissue T.

Circuitry relating to providing power and data to the image capture device 525 (not shown in FIG. 5) can be provided as it would be to other endoscopes typically used in conjunction with minimally invasive surgical procedures and systems.

In various exemplary embodiments, the light sources that may be used in conjunction with the optical sensing modules and image capture devices of the present disclosure may generate light in various ways such as, but not limited to, electron-stimulation, incandescent lamps, light emitting diodes, electroluminescence, gas discharge, high-intensity discharge, lasers, chemoluminescence, fluorescence, and/or phosphorescence. It is contemplated as within the scope of the present disclosure that the light is guided through fiber optic cables or light pipes (not shown), or that a plurality of light sources is used.

In the exemplary embodiments of FIGS. 4 and 5, desirable properties of the transparent material used in the jaw members may include, for example, being optically clear, hydrophobic, and/or antireflective. These properties can be attained through material selection or by treating the material, such as with the application of a coating. Depending on the intended application of the surgical instrument, the transparent material is sterilizable and/or autoclavable, for example, when repeat use of the instrument is desired. In some cases, surface features, such as teeth or other non-smooth surface profiles or fenestrations, are provided on the grasping side surface of the transparent material in order to facilitate grip or reduce trauma; however, in other applications, a smooth surface may be desirable. Further, while providing the transparent portion as a material is shown and described above, those having ordinary skill in the art would appreciate that an opening without a material covering the opening could also be used as the transparent portion of the jaw member. Indeed, some conventional surgical instrument grasping devices are provided with such an opening (fenestration).

Aside from surface features, the overall curvature of the transparent portion may be selected as desired. For example, the transparent portion can have a flat grasping surface that can compress tissue to remove natural curvature from the tissue during gripping, which may facilitate image capture and processing. In other situations, the transparent portion can have a curved surface on one or both sides of the transparent portion. In other exemplary embodiments, the transparent portion can be recessed away from the tissue slightly as compared to other non-transparent portions of the jaw member.

Various indicia, such as one or more etchings, imprints, laser cut markings, etc. can be provided on the transparent portion(s) of the jaw member. Such indicia can serve as a fixed reference by which to assist in the image processing and comparison of image data.

As discussed above, in the exemplary embodiments of FIGS. 4 and 5, only one jaw member is depicted. Those having ordinary skill in the art would recognize that the surgical instruments in accordance with the present disclosure can include a second jaw member of similar configuration, or alternatively a second jaw member without an image capture device, depending on the particular applications for which the surgical instrument may be desired. For example, in applications for which the tissue being grabbed is relatively dense, it may be desirable to enable image capture from both jaw members so as to be able to image both "sides" of the gripped tissue, and/or to allow a user flexibility in choosing the jaw member from which to capture images. In cases where two image capture devices are provided (such as being integrated with each jaw member), it is contemplated that the devices may be separately controlled. However, the ability to use only one jaw with an imaging device can provide less complexity in overall instrument specifications, design, and use.

As noted above, various embodiments disclosed herein contemplate being used with teleoperated computer-assisted surgery. Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment.

The teleoperated computer-assisted surgical systems may be employed with one or more consoles that are in or adjacent to the operating theater or located in a remote location.

Exemplary teleoperated, computer-assisted surgical systems (sometimes referred to as robotic surgical systems) with which exemplary embodiments of the present disclosure may be implemented include those described in, for example, U.S. Patent App. Pub. No. US 2013/0325033 A1 (published Dec. 5, 2013), entitled "Multi-Port Surgical Robotic System Architecture," U.S. Patent App. Pub. No. US 2013/0325031 A1 (published Dec. 5, 2013), entitled "Redundant Axis and Degree of Freedom for Hardware-Constrained Remote Center Robotic Manipulator," and U.S. Pat. No. 8,852,208 (issued Oct. 7, 2014), entitled "Surgical System Instrument Mounting," and U.S. Pat. No. 8,545,515 (issued Oct. 1, 2013), entitled Curved Cannula Surgical System, each of which is hereby incorporated by reference in its entirety. Further, the exemplary embodiments described herein may be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc. Although the above references discuss surgical instruments and other devices related to a patient side cart of a teleoperated surgical system, the present disclosure is not limited to use with surgical instruments for a teleoperated surgical system, but rather extends to manually operated surgical instruments/systems.

Further, exemplary embodiments using controllers and processors can be implemented in computing hardware (computing apparatus) and/or software, such as (in a non-limiting example) any computer that can store, retrieve, process and/or output data and/or communicate with other computers. The results produced can be shown on a display of the computing hardware or a separate display operably coupled to such hardware. One or more programs/software comprising algorithms to effect the various responses and signal processing in accordance with various exemplary embodiments of the present disclosure can be implemented by a processor of or in conjunction with an electronics/control console, such as is generally one of the core components of a teleoperated computer-assisted surgical system, and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A medical apparatus comprising:
a shaft; and
a jaw assembly coupled to the shaft,
the jaw assembly comprising a first jaw member and a second jaw member,
the first jaw member comprising a first gripping surface, an exterior surface reverse of the first gripping surface, and a transparent portion spanning a thickness of the first jaw member from the first gripping surface to the exterior surface, and
the second jaw member comprising a second gripping surface opposing the first gripping surface,
wherein the jaw assembly is configured to grasp material between the first and second gripping surfaces;
a sensor configured to sense light transmitted through the transparent portion; and
a controller operably coupled to the sensor, the controller configured to process sensed data captured by the sensor,
wherein the controller is operably coupled to the jaw assembly and configured to output a control command to alter a grip exerted by the jaw assembly based on processing the sensed data captured by the sensor.

2. The medical apparatus of claim 1, wherein the sensor is positioned at a location external to the jaw assembly.

3. The medical apparatus of claim 2, wherein the controller is configured to process the sensed data captured by the sensor using optical flow, digital image correlation, or both optical flow and digital image correlation.

4. The medical apparatus of claim 1, wherein the controller is configured to detect deformation, detect slip, or both detect deformation and detect slip of material grasped by the jaw assembly based on sensed data captured by the sensor.

5. The medical apparatus of claim 4, further comprising:
a feedback mechanism operably coupled to the controller;
wherein the feedback mechanism is configured to provide feedback indicative of detection of deformation by the controller, provide feedback indicative of detection of slip by the controller, or provide both feedback indicative of detection of deformation by the controller and feedback indicative of detection of slip by the controller.

6. The medical apparatus of claim 4, wherein the controller is configured to output a control command to alter a grip exerted by the jaw assembly in response to detecting deformation or slip of material grasped by the jaw assembly.

7. The medical apparatus of claim 6, wherein the controller is configured to output, in response to detecting deformation of material grasped by the jaw assembly, a control command to decrease a gripping force exerted by the jaw assembly.

8. The medical apparatus of claim 6, wherein the controller is configured to output, in response to detecting slip of material grasped by the jaw assembly, a control command to increase a gripping force applied by the jaw assembly.

9. The medical apparatus of claim 1, wherein the transparent portion is configured such that an image capture device positioned at a location external to the jaw assembly can capture images, through the transparent portion, of material grasped between the first and second gripping surfaces.

10. The medical apparatus of claim 1, further comprising:
an image capture device positioned at a location external to the jaw assembly,
the image capture device comprising the sensor and being configured to capture images, through the transparent portion, of material grasped between the first and second gripping surfaces; and
wherein the controller is configured to process images captured by the image capture device of material grasped by the jaw assembly to detect deformation, detect slip, or both detect deformation and detect slip of the material.

11. The medical apparatus of claim 1:
wherein the first jaw member extends in a longitudinal direction distally from the shaft; and
wherein the thickness of the first jaw member extends in a direction perpendicular to the longitudinal direction.

12. The medical apparatus of claim 1, wherein the transparent portion comprises glass or plastic.

13. The medical apparatus of claim 1, wherein the transparent portion comprises one or more indicia.

14. A medical apparatus comprising:
a shaft;
a jaw assembly coupled to the shaft, the jaw assembly comprising a first jaw member and a second jaw member,
the first jaw member comprising a first gripping surface and a transparent portion,
at least a portion of the first gripping surface being part of the transparent portion,
the second jaw member comprising a second gripping surface opposing the first gripping surface, and
the jaw assembly configured to grasp material between the first and second gripping surfaces;
an image capture device positioned at a location external to the jaw assembly to capture images, through the transparent portion, of a region between the first and second gripping surfaces; and
a controller operably coupled to the image capture device to receive image data corresponding to images captured by the image capture device;
wherein the controller is configured to, on condition of material being grasped by the jaw assembly, process the received image data to detect deformation of the material being grasped by the jaw assembly, detect slip of the material being grasped by the jaw assembly, or both detect deformation and detect slip of the material being grasped by the jaw assembly.

15. The medical apparatus of claim 14, wherein the controller is configured to process the received image data using optical flow, digital image correlation, or both optical flow and digital image correlation.

16. The medical apparatus of claim 14, wherein the controller is configured to, responsive to detecting deformation of the material being grasped by the jaw assembly, output a control command to decrease a gripping force applied by the jaw assembly.

17. The medical apparatus of claim 14, wherein the controller is configured to, responsive to detecting slip of the material being grasped by the jaw assembly, output a control command to increase a gripping force applied by the jaw assembly.

18. The medical apparatus of claim 14, wherein the controller is operably coupled to the jaw assembly and configured to output a control command to alter a grip exerted by the jaw assembly in response to detecting deformation or slip of material grasped by the jaw assembly.

19. A medical apparatus comprising:
a shaft; and
a jaw assembly coupled to the shaft,
   the jaw assembly comprising a first jaw member and a second jaw member,
   the first jaw member comprising a first gripping surface, an exterior surface reverse of the first gripping surface, and a transparent portion spanning a thickness of the first jaw member from the first gripping surface to the exterior surface, and
   the second jaw member comprising a second gripping surface opposing the first gripping surface,
   wherein the jaw assembly is configured to grasp material between the first and second gripping surfaces;
a sensor at a location external to the jaw assembly and configured to sense light transmitted through the transparent portion; and
a controller operably coupled to the sensor, the controller configured to detect deformation, detect slip, or both detect deformation and detect slip of material grasped by the jaw assembly based on sensed data captured by the sensor,
wherein the controller is operably coupled to the jaw assembly and configured to output a control command to alter a grip exerted by the jaw assembly in response to detecting deformation or slip of material grasped by the jaw assembly.

20. The medical apparatus of claim 19, wherein the controller is configured to process the sensed data captured by the sensor using optical flow, digital image correlation, or both optical flow and digital image correlation.

21. The medical apparatus of claim 19, wherein the controller is configured to detect deformation, detect slip, or both detect deformation and detect slip of material grasped by the jaw assembly by using optical flow, digital image correlation, or both optical flow and digital image correlation to process the sensed data captured by the sensor.

22. A medical apparatus comprising:
a shaft; and
a jaw assembly coupled to the shaft,
   the jaw assembly comprising a first jaw member and a second jaw member,
   the first jaw member comprising a first gripping surface, an exterior surface reverse of the first gripping surface, and a transparent portion spanning a thickness of the first jaw member from the first gripping surface to the exterior surface, and
   the second jaw member comprising a second gripping surface opposing the first gripping surface,
   wherein the jaw assembly is configured to grasp material between the first and second gripping surfaces, and
   wherein the transparent portion is configured such that an image capture device positioned at a location external to the jaw assembly can capture images, through the transparent portion, of material grasped between the first and second gripping surfaces.

* * * * *